US006171841B1

(12) United States Patent
Akira et al.

(10) Patent No.: US 6,171,841 B1
(45) Date of Patent: Jan. 9, 2001

(54) DNA CODING FOR SERINE/THREONINE KINASE

(75) Inventors: Shizuo Akira, Osaka; Taro Kawai, Hyogo, both of (JP)

(73) Assignee: Japan Science and Technology Corporation, Kawaguchi (JP)

( * ) Notice: Under 35 U.S.C. 154(b), the term of this patent shall be extended for 0 days.

(21) Appl. No.: 09/186,277

(22) Filed: Nov. 5, 1998

Related U.S. Application Data

(62) Division of application No. 09/159,385, filed on Sep. 23, 1998, now Pat. No. 5,958,748.

(30) Foreign Application Priority Data

Sep. 26, 1997 (JP) .................................... 9-261589

(51) Int. Cl.[7] .............................. C12N 9/12; C07H 21/04
(52) U.S. Cl. ............... 435/194; 435/252.33; 435/254.11; 435/320.1; 536/23.1; 536/23.2; 536/23.5
(58) Field of Search ............................... 435/194, 252.33, 435/254.11, 320.1; 536/23.1, 23.2, 23.5

(56) References Cited

PUBLICATIONS

Chien et al.; "The two–hybrid system: A method to identify and clone genes for proteins that interact with a protein of interest"; Proceedings of the National Academy of Sciences of USA; vol. 88; Nov. 1, 1991; pp. 9578–9582; XP000647704.

Holzman et al.; "Identification, .molecular cloning, and characterization of dual leucine zipper bearing kinase"; vol. 269, No. 49; 1994; pp. 30808–30817; XP002120730.

Kawai et al.; "ZIP kinase, a novel serine/threonine kinase which mediates apoptosis"; Molecular and Cellular Biology; vol. 18, No. 3; Mar. 1998; pp. 1642–1651; XP002120731.

Hillier et al.; "*Homo sapiens* cDNA clone similar to DAP kinase"; EMBL Database Entry HS936258; Accession No. N23936; Dec. 30, 1995; Abstract; XP002120726.

Strausberg; "*Homo sapiens* cDNA clone similar to DAP kinase"; EMBL Database Entry AA557328; Accession No. AA557328; Sep. 11, 1997; Abstract; XP002120727.

Marra et al.; "*Mus musculus* cDNA clone similar to DAP kinase"; EMBL Database Entry MMAA13041; Accession No. AA22667; Feb. 3, 1997; Abstract; XP002120729.

*Primary Examiner*—Nashaat Nashed
(74) *Attorney, Agent, or Firm*—Foley & Lardner

(57) ABSTRACT

The nucleic acid sequence encoding mammalian serine/threonine protein kinase comprising a leucine zipper motif (Zip-kinase) and the corresponding amino acid sequence are disclosed. The Zip-kinase is a nuclear enzyme having activity of inducing apoptosis. A victor and a transformed cell with the nucleic acid sequence as well as recombinant method of making the Zip-kinase utilizing the transformed cell are taught.

10 Claims, 10 Drawing Sheets

(2 of 10 Drawing Sheet(s) Filed in Color)

FIG. 1

| | | |
|---|---|---|
| mouse ZIP-kinase | MSTFRQEDVEDHYEMGEELGSGQFAIVRKCQQKGTGMEYAAKFIKKRRLPSSRRGVSREE | 60 |
| human ZIP-kinase | MSTFRQEDVEDHYEMGEELGSGQFAIVRKCRQKGTGKEYAAKFIKKRRLSSSRRGVSREE | 60 |
| mouse ZIP-kinase | IEREVSILREIRHPNIITLHDVFENKTDVVLIELVSGGELFDFLAEKESLTEDEATQFL | 120 |
| human ZIP-kinase | IEREVNILREIRHPNIITLHDIFENKTDVVLIELVSGGELFDFLAEKESLTEDEATQFL | 120 |
| mouse ZIP-kinase | KQILDGVHYLHSKRIAHFDLKPENIMLLDKHAASPRIKLIDFGIAHRIEAGSEFKNIFGT | 180 |
| human ZIP-kinase | KQILDGVHYLHSKRIAHFDLKPENIMLLDKNVPNPRIKLIDFGIAHKIEAGNEFKNIFGT | 180 |
| mouse ZIP-kinase | PEFVAPEIVNYEPLGLEADMWSIGVITYILLSGASPFLGETKQETLTNISAVNYDFDEEY | 240 |
| human ZIP-kinase | PEFVAPEIVNYEPLGLEADMWSIGVITYILLSGASPFLGETKQETLTNISAVNYDFDEEY | 240 |
| mouse ZIP-kinase | FSSTSELAKDFIRRLLVKDPKRRMTIAQSLEHSWIK-VRRR----EDGARKPERRRLRAA | 295 |
| human ZIP-kinase | FSNTSELAKDFIRRLLVKDPKRRMTIAQSLEHSWIKAIRRRNVRGEDSGRKPERRRLKTT | 300 |
| mouse ZIP-kinase | RLREYSLKSHSSMPRNTSYASFERFSRVLEDVAAAEEQGLRELQRGRRQCRERVCALRAAA | 355 |
| human ZIP-kinase | RLKEYTIKSHSSLPPNNSYADFERFSKVLEEAAAAEEGLRELQRSRRLCHEDVEALAAIY | 360 |
| mouse ZIP-kinase | EQREARCRDGSAGLGRDLRRLRTELGRTEALRTRAQQEEARRAALLGAGGLKRRLCRLENRY | 415 |
| human ZIP-kinase | EEKEAWYREESDSLGQDLRRLRQELLKTEALKRQAQQEEAKGALLGTSGLKRRFSRLENRY | 420 |
| mouse ZIP-kinase | DALAAQVAAEVQFMRDLVRALEQERLQA-ECGVR | 448 |
| human ZIP-kinase | EALAKQVASEMRFVQDLVRALEQEKLQGVECGLR | 454 |

Protein kinase domain →
Leucine zipper domain

FIG. 2

| | | | | | | |
|---|---|---|---|---|---|---|
| mouse ZIP-kinase | 1: | MSTFRQEDVEDHYEMGEELGSGQFA | IVRKCQQKGTGMEYAAKFIK | KRRLPSSRRGVSR | 58 |
| human ZIP-kinase | 1: | MSTFRQEDVEDHYEMGEELGSGQFA | IVRKCRQKGTGKEYAAKFIK | KRRLSSSRRGVSR | 58 |
| mouse DAP-kinase | 1: | MTVFRQENVDDYYDTGEELGSGQFA | VVKKCREKSTGLQYAAKFIK | KRRTKSSRRGVSR | 60 |
| human DAP-kinase | 1: | MTVFRQENVDDYYDTGEELGSGQFA | VVKKCREKSIGLQYPAKFIK | KRRTKSSRRGVSR | 58 |

I

| mouse ZIP-kinase | 59: | EIEREVSILREIRHPNIITLHDVF | ENKTDVVLILELVSGGELFD | F-LAEKESLTEDEA | 116 |
| human ZIP-kinase | 59: | EIEREVNILREIRHPNIITLHDIF | ENKTDVVLILELVSGGELFD | F-LAEKESLTEDEA | 116 |
| mouse DAP-kinase | 61: | EDIEREVSILKEIRHPNVITLHEV | YENKTDVILILELVAGGELFD | FFTLAEKESLTEEEA | 120 |
| human DAP-kinase | 59: | EDIEREVSILKEIQHPNVITLHEV | YENKTDVILILELVAGGELFD | F-LAEKESLTEEEA | 116 |

III      IV      V

| mouse ZIP-kinase | 117: | TQFLKQIIDGVHYLHSKR | IAHFDLKPENIMLLDKHAASPRIKL | IDFG | --IAHRIEAGSEF | 174 |
| human ZIP-kinase | 117: | TQFLKQIIDGVHYLHSKR | IAHFDLKPENIMLLDKNVPNPRIKL | IDFG | --IAHKIEAGNEF | 174 |
| mouse DAP-kinase | 121: | TEFLKQILSGVYYLHSLQ | IAHFDLKPENIMLLDKRNVPKPRIKI | IDFGFTLAHKIDFGNEF | 180 |
| human DAP-kinase | 117: | IEFLKQIINGVYYLHSLQ | IAHFDLKPENIMLLDKRNVPKPRIKI | IDFG | -----NEF | 166 |

VIa      VIb      VII

| mouse ZIP-kinase | 175: | KNIFGTPEFVAPEIVNYEPLGLEADMWS | IGVITYILLSGASPFLGETK | --QETLTNISAV | 232 |
| human ZIP-kinase | 175: | KNIFGTPEFVAPEIVNYEPLGLEADMWS | IGVITYILLSGASPFLGETK | --QETLTNISAV | 232 |
| mouse DAP-kinase | 181: | KNIFGTPEFVAPEIVNYEPLGLEADMWS | IGVITYILLSGASPFLGDIK | FTQETLANVSAV | 240 |
| human DAP-kinase | 167: | KNIFGTPEFVAPEIVNYEPLGLEADMWS | IGVITYILLSGASPFLGDIK | --QETLANVSAV | 224 |

VIII      IX      X

| mouse ZIP-kinase | 233: | NYDFDEEYFSSTSELAKDFIRRLLVKDPKRKRMT | IAQSLEHSWIK | ----V---R---R- | 280 |
| human ZIP-kinase | 233: | NYDFDEEYFSNISELAKDFIRRLLVKDPKRKRMT | IAQSLEHSWIK | ----IR---RNVRG | 285 |
| mouse DAP-kinase | 241: | NYDFEEFFRNTSTLAKDFIRRLLVKDPKKKRMT | IAQSLEHSWIKA | IR---RNVRG | 300 |
| human DAP-kinase | 225: | NVEFEDEYFSNTSALAKDFIRRLLVKDPKKKRMT | IQDSLQHPWIK | PKDTQFTQALSRKASA | 282 |

XI

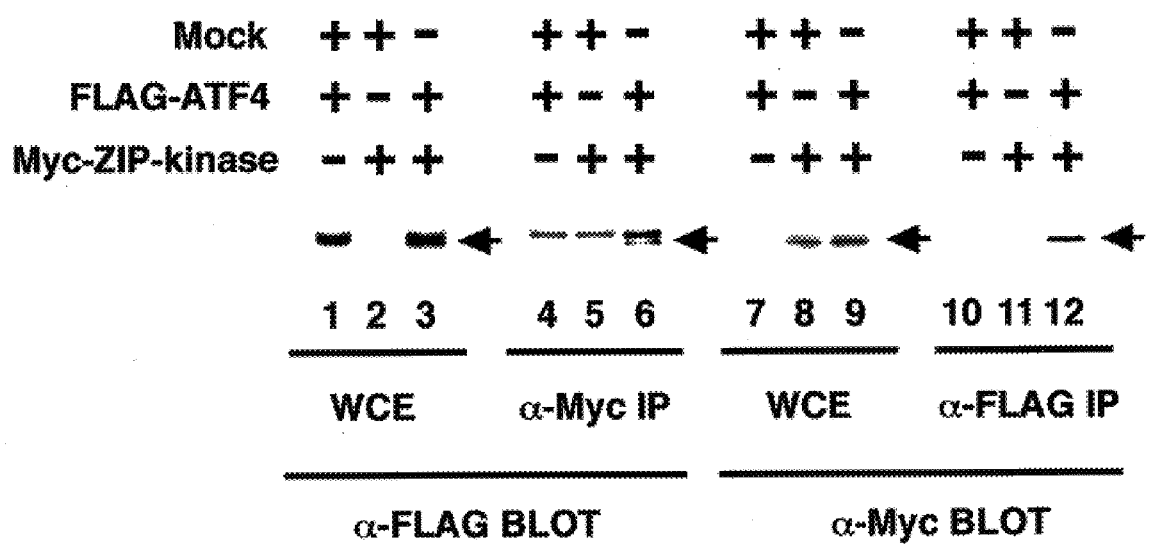

FIG. 6

| GAL4 DNA Binding Domain | GAL4 Activation Domain | His⁺ Trp⁻ Leu⁻ | His⁻ Trp⁻ Leu⁻ |
|---|---|---|---|
| ZIP-kinase LZ (398-448) | Mock | ● | |
| | ZIP-kinase LZ (398-448) | ● | ● |
| | ZIP-kinase LA (398-448) | ● | |

FIG. 7
Mock
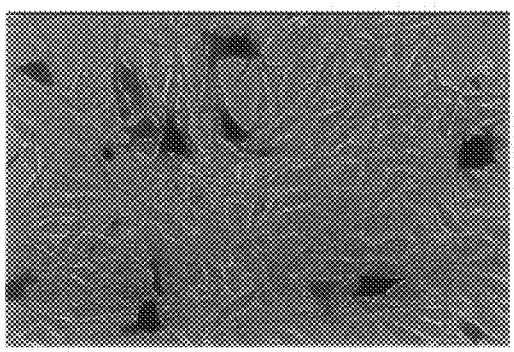
ZIP-kinase
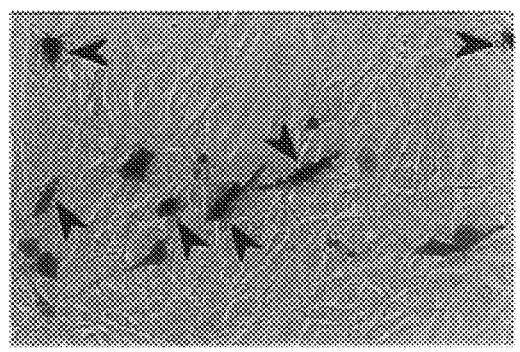
ZIP-kinase K42A
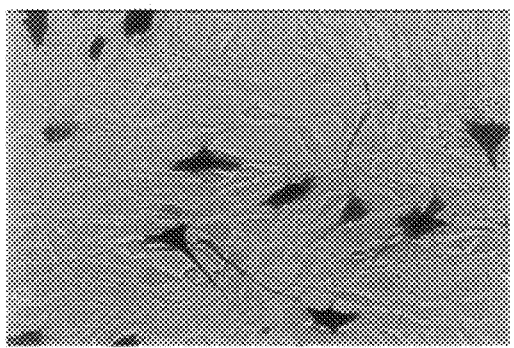
ZIP-kinase LA
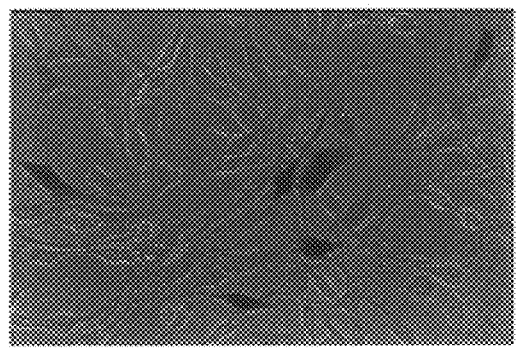

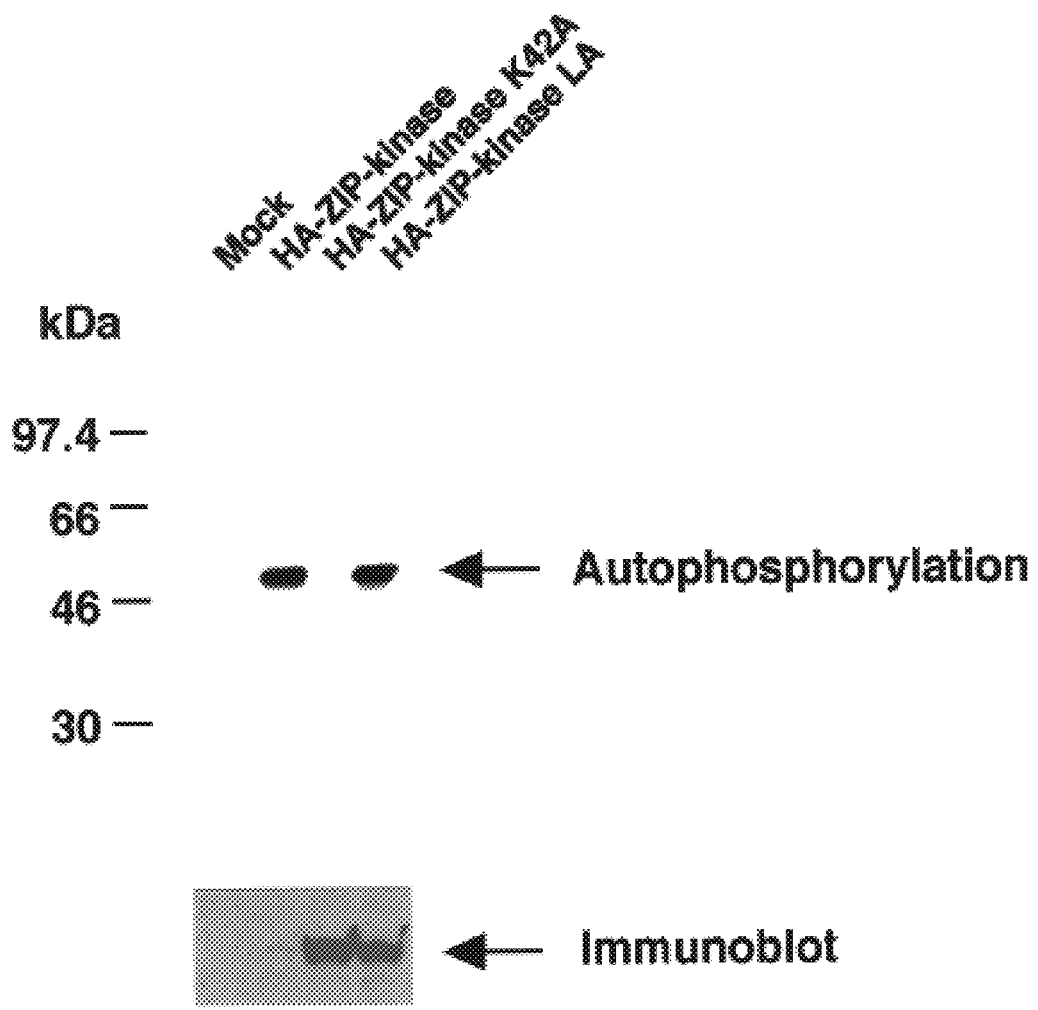

FIG. 10A
FLAG-ATF4
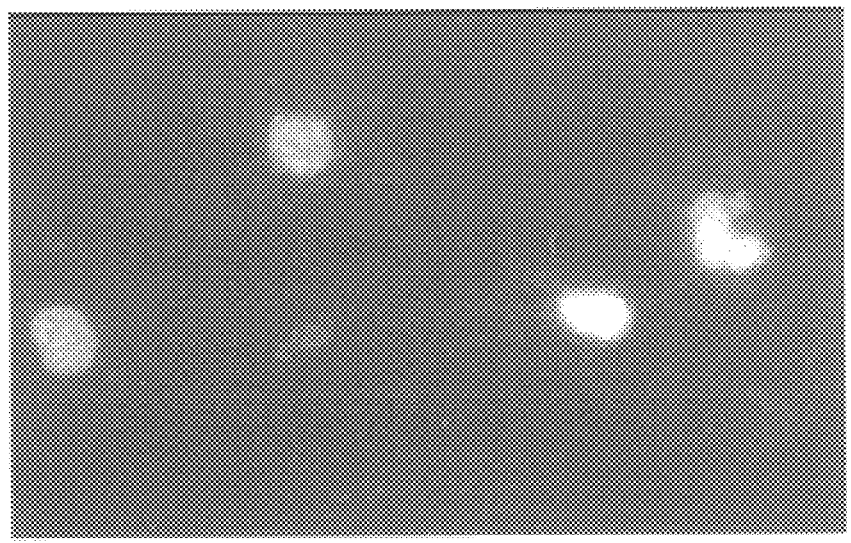
FLAG-ZIP-kinase K42A
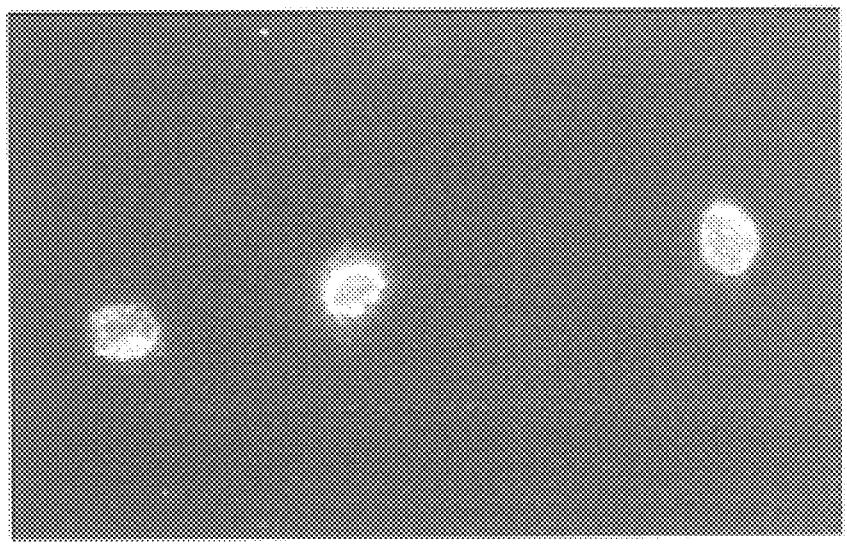
FIG. 10B

SEQUENCE LISTING

<160> NUMBER OF SEQ ID NOS: 8

<210> SEQ ID NO 1
<211> LENGTH: 454
<212> TYPE: PRT
<213> ORGANISM: Homo sapiens

<400> SEQUENCE: 1

```
Met Ser Thr Phe Arg Gln Glu Asp Val Glu Asp His Tyr Glu Met Gly
 1               5                  10                  15

Glu Glu Leu Gly Ser Gly Gln Phe Ala Ile Val Arg Lys Cys Arg Gln
            20                  25                  30

Lys Gly Thr Gly Lys Glu Tyr Ala Ala Lys Phe Ile Lys Lys Arg Arg
        35                  40                  45

Leu Ser Ser Ser Arg Arg Gly Val Ser Arg Glu Glu Ile Glu Arg Glu
    50                  55                  60

Val Asn Ile Leu Arg Glu Ile Arg His Pro Asn Ile Ile Thr Leu His
65                  70                  75                  80

Asp Ile Phe Glu Asn Lys Thr Asp Val Val Leu Ile Leu Glu Leu Val
                85                  90                  95

Ser Gly Gly Glu Leu Phe Asp Phe Leu Ala Glu Lys Glu Ser Leu Thr
            100                 105                 110

Glu Asp Glu Ala Thr Gln Phe Leu Lys Gln Ile Leu Asp Gly Val His
        115                 120                 125

Tyr Leu His Ser Lys Arg Ile Ala His Phe Asp Leu Lys Pro Glu Asn
    130                 135                 140

Ile Met Leu Leu Asp Lys Asn Val Pro Asn Pro Arg Ile Lys Leu Ile
145                 150                 155                 160

Asp Phe Gly Ile Ala His Lys Ile Glu Ala Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Glu Thr Lys Gln Glu
    210                 215                 220

Thr Leu Thr Asn Ile Ser Ala Val Asn Tyr Asp Phe Asp Glu Glu Tyr
225                 230                 235                 240
```

-continued

```
Phe Ser Asn Thr Ser Glu Leu Ala Lys Asp Phe Ile Arg Arg Leu Leu
                245                 250                 255

Val Lys Asp Pro Lys Arg Arg Met Thr Ile Ala Gln Ser Leu Glu His
            260                 265                 270

Ser Trp Ile Lys Ala Ile Arg Arg Asn Val Arg Gly Glu Asp Ser
        275                 280                 285

Gly Arg Lys Pro Glu Arg Arg Leu Lys Thr Thr Arg Leu Lys Glu
    290                 295                 300

Tyr Thr Ile Lys Ser His Ser Ser Leu Pro Pro Asn Asn Ser Tyr Ala
305                 310                 315                 320

Asp Phe Glu Arg Phe Ser Lys Val Leu Glu Glu Ala Ala Ala Glu
                325                 330                 335

Glu Gly Leu Arg Glu Leu Gln Arg Ser Arg Arg Leu Cys His Glu Asp
                340                 345                 350

Val Glu Ala Leu Ala Ala Ile Tyr Glu Glu Lys Glu Ala Trp Tyr Arg
            355                 360                 365

Glu Glu Ser Asp Ser Leu Gly Gln Asp Leu Arg Arg Leu Arg Gln Glu
        370                 375                 380

Leu Leu Lys Thr Glu Ala Leu Lys Arg Gln Ala Gln Glu Glu Ala Lys
385                 390                 395                 400

Gly Ala Leu Leu Gly Thr Ser Gly Leu Lys Arg Arg Phe Ser Arg Leu
                405                 410                 415

Glu Asn Arg Tyr Glu Ala Leu Ala Lys Gln Val Ala Ser Glu Met Arg
            420                 425                 430

Phe Val Gln Asp Leu Val Arg Ala Leu Glu Gln Glu Lys Leu Gln Gly
                435                 440                 445

Val Glu Cys Gly Leu Arg
    450

<210> SEQ ID NO 2
<211> LENGTH: 448
<212> TYPE: PRT
<213> ORGANISM: Mus musculus

<400> SEQUENCE: 2

Met Ser Thr Phe Arg Gln Glu Asp Val Glu Asp His Tyr Glu Met Gly
1               5                   10                  15

Glu Glu Leu Gly Ser Gly Gln Phe Ala Ile Val Arg Lys Cys Gln Gln
                20                  25                  30

Lys Gly Thr Gly Met Glu Tyr Ala Ala Lys Phe Ile Lys Lys Arg Arg
            35                  40                  45

Leu Pro Ser Ser Arg Arg Gly Val Ser Arg Glu Ile Glu Arg Glu
    50                  55                  60

Val Ser Ile Leu Arg Glu Ile Arg His Pro Asn Ile Ile Thr Leu His
65                  70                  75                  80

Asp Val Phe Glu Asn Lys Thr Asp Val Val Leu Ile Leu Glu Leu Val
                85                  90                  95

Ser Gly Gly Glu Leu Phe Asp Phe Leu Ala Glu Lys Glu Ser Leu Thr
            100                 105                 110

Glu Asp Glu Ala Thr Gln Phe Leu Lys Gln Ile Leu Asp Gly Val His
        115                 120                 125

Tyr Leu His Ser Lys Arg Ile Ala His Phe Asp Leu Lys Pro Glu Asn
    130                 135                 140

Ile Met Leu Leu Asp Lys His Ala Ala Ser Pro Arg Ile Lys Leu Ile
145                 150                 155                 160
```

-continued

```
Asp Phe Gly Ile Ala His Arg Ile Glu Ala Gly Ser Glu Phe Lys Asn
                165                 170                 175
Ile Phe Gly Thr Pro Glu Phe Val Ala Pro Glu Ile Val Asn Tyr Glu
            180                 185                 190
Pro Leu Gly Leu Glu Ala Asp Met Trp Ser Ile Gly Val Ile Thr Tyr
        195                 200                 205
Ile Leu Leu Ser Gly Ala Ser Pro Phe Leu Gly Glu Thr Lys Gln Glu
    210                 215                 220
Thr Leu Thr Asn Ile Ser Ala Val Asn Tyr Asp Phe Asp Glu Glu Tyr
225                 230                 235                 240
Phe Ser Ser Thr Ser Glu Leu Ala Lys Asp Phe Ile Arg Arg Leu Leu
                245                 250                 255
Val Lys Asp Pro Lys Arg Arg Met Thr Ile Ala Gln Ser Leu Glu His
            260                 265                 270
Ser Trp Ile Lys Val Arg Arg Glu Asp Gly Ala Arg Lys Pro Glu
        275                 280                 285
Arg Arg Arg Leu Arg Ala Ala Arg Leu Arg Glu Tyr Ser Leu Lys Ser
    290                 295                 300
His Ser Ser Met Pro Arg Asn Thr Ser Tyr Ala Ser Phe Glu Arg Phe
305                 310                 315                 320
Ser Arg Val Leu Glu Asp Val Ala Ala Glu Gln Gly Leu Arg Glu
                325                 330                 335
Leu Gln Arg Gly Arg Arg Gln Cys Arg Glu Arg Val Cys Ala Leu Arg
            340                 345                 350
Ala Ala Ala Glu Gln Arg Glu Ala Arg Cys Arg Asp Gly Ser Ala Gly
        355                 360                 365
Leu Gly Arg Asp Leu Arg Arg Leu Arg Thr Glu Leu Gly Arg Thr Glu
    370                 375                 380
Ala Leu Arg Thr Arg Ala Gln Glu Glu Ala Arg Ala Ala Leu Leu Gly
385                 390                 395                 400
Ala Gly Gly Leu Lys Arg Arg Leu Cys Arg Leu Glu Asn Arg Tyr Asp
                405                 410                 415
Ala Leu Ala Ala Gln Val Ala Ala Glu Val Gln Phe Val Arg Asp Leu
            420                 425                 430
Val Arg Ala Leu Glu Gln Glu Arg Leu Gln Ala Glu Cys Gly Val Arg
        435                 440                 445

<210> SEQ ID NO 3
<211> LENGTH: 2132
<212> TYPE: DNA
<213> ORGANISM: Homo sapiens
<220> FEATURE:
<221> NAME/KEY: CDS
<222> LOCATION: (94)..(1455)

<400> SEQUENCE: 3
gttgccatta ggggactcct gaggtcctat ctccaggctg cggtgactgc actttccctg     60
gagtggaagc tgctggaagg cggaccggcc gcc atg tcc acg ttc agg cag gag    114
                                    Met Ser Thr Phe Arg Gln Glu
                                      1               5 gac gtg gag gac cat tat gag atg ggg gag gag ctg ggc agc ggc cag    162
Asp Val Glu Asp His Tyr Glu Met Gly Glu Glu Leu Gly Ser Gly Gln
         10                  15                  20 ttt gcg atc gtg cgg aag tgc cgg cag aag ggc acg ggc aag gag tac    210
Phe Ala Ile Val Arg Lys Cys Arg Gln Lys Gly Thr Gly Lys Glu Tyr
     25                  30                  35
```

-continued

```
gca gcc aag ttc atc aag aag cgc cgc ctg tca tcc agc cgg cgt ggg     258
Ala Ala Lys Phe Ile Lys Lys Arg Arg Leu Ser Ser Ser Arg Arg Gly
 40              45                  50                  55 gtg agc cgg gag gag atc gag cgg gag gtg aac atc ctg cgg gag atc     306
Val Ser Arg Glu Glu Ile Glu Arg Glu Val Asn Ile Leu Arg Glu Ile
                 60                  65                  70 cgg cac ccc aac atc atc acc ctg cac gac atc ttc gag aac aag acg     354
Arg His Pro Asn Ile Ile Thr Leu His Asp Ile Phe Glu Asn Lys Thr
             75                  80                  85 gac gtg gtc ctc atc ctg gag ctg gtc tct ggc ggg gag ctc ttt gac     402
Asp Val Val Leu Ile Leu Glu Leu Val Ser Gly Gly Glu Leu Phe Asp
         90                  95                 100 ttc ctg gcg gag aaa gag tcg ctg acg gag gac gag gcc acc cag ttc     450
Phe Leu Ala Glu Lys Glu Ser Leu Thr Glu Asp Glu Ala Thr Gln Phe
     105                 110                 115 ctc aag cag atc ctg gac ggc gtt cac tac ctg cac tct aag cgc atc     498
Leu Lys Gln Ile Leu Asp Gly Val His Tyr Leu His Ser Lys Arg Ile
120                 125                 130                 135 gca cac ttt gac ctg aag ccg gaa aac atc atg ctg ctg gac aag aac     546
Ala His Phe Asp Leu Lys Pro Glu Asn Ile Met Leu Leu Asp Lys Asn
                 140                 145                 150 gtg ccc aac cca cga atc aag ctc atc gac ttc ggc atc gcg cac aag     594
Val Pro Asn Pro Arg Ile Lys Leu Ile Asp Phe Gly Ile Ala His Lys
             155                 160                 165 atc gag gcg ggg aac gag ttc aag aac atc ttc ggc acc ccg gag ttt     642
Ile Glu Ala Gly Asn Glu Phe Lys Asn Ile Phe Gly Thr Pro Glu Phe
         170                 175                 180 gtg gcc cca gag att gtg aac tat gag ccg ctg ggc ctg gag gcg gac     690
Val Ala Pro Glu Ile Val Asn Tyr Glu Pro Leu Gly Leu Glu Ala Asp
     185                 190                 195 atg tgg agc atc ggt gtc atc acc tat atc ctc ctg agc ggt gca tcc     738
Met Trp Ser Ile Gly Val Ile Thr Tyr Ile Leu Leu Ser Gly Ala Ser
200                 205                 210                 215 ccg ttc ctg ggc gag acc aag cag gag acg ctc acc aac atc tca gcc     786
Pro Phe Leu Gly Glu Thr Lys Gln Glu Thr Leu Thr Asn Ile Ser Ala
                 220                 225                 230 gtg aac tac gac ttc gac gag gag tac ttc agc aac acc agc gag ctg     834
Val Asn Tyr Asp Phe Asp Glu Glu Tyr Phe Ser Asn Thr Ser Glu Leu
             235                 240                 245 gcc aag gac ttc att cgc cgg ctg ctc gtc aaa gat ccc aag cgg aga     882
Ala Lys Asp Phe Ile Arg Arg Leu Leu Val Lys Asp Pro Lys Arg Arg
         250                 255                 260 atg acc att gcc cag agc ctg gaa cat tcc tgg att aag gcg atc cgg     930
Met Thr Ile Ala Gln Ser Leu Glu His Ser Trp Ile Lys Ala Ile Arg
     265                 270                 275 cgg cgg aac gtg cgt ggt gag gac agc ggc cgc aag ccc gag cgg cgg     978
Arg Arg Asn Val Arg Gly Glu Asp Ser Gly Arg Lys Pro Glu Arg Arg
280                 285                 290                 295 cgc ctg aag acc acg cgt ctg aag gag tac acc atc aag tcg cac tcc    1026
Arg Leu Lys Thr Thr Arg Leu Lys Glu Tyr Thr Ile Lys Ser His Ser
                 300                 305                 310 agc ttg ccg ccc aac aac agc tac gcc gac ttc gag cgc ttc tcc aag    1074
Ser Leu Pro Pro Asn Asn Ser Tyr Ala Asp Phe Glu Arg Phe Ser Lys
             315                 320                 325 gtg ctg gag gag gcg gcg gcc gcc gag gag ggc ctg cgc gag ctg cag    1122
Val Leu Glu Glu Ala Ala Ala Ala Glu Glu Gly Leu Arg Glu Leu Gln
         330                 335                 340 cgc agc cgg cgg ctc tgc cac gag gac gtg gag gcg ctg gcc gcc atc    1170
Arg Ser Arg Arg Leu Cys His Glu Asp Val Glu Ala Leu Ala Ala Ile
```

-continued

```
              345                 350                 355
tac gag gag aag gag gcc tgg tac cgc gag gag agc gac agc ctg ggc        1218
Tyr Glu Glu Lys Glu Ala Trp Tyr Arg Glu Glu Ser Asp Ser Leu Gly
360                 365                 370                 375 cag gac ctg cgg agg cta cgg cag gag ctg ctc aag acc gag gcg ctc        1266
Gln Asp Leu Arg Arg Leu Arg Gln Glu Leu Leu Lys Thr Glu Ala Leu
                380                 385                 390 aag cgg cag gcg cag gag gag gcc aag ggc gcg ctg ctg ggg acc agc        1314
Lys Arg Gln Ala Gln Glu Glu Ala Lys Gly Ala Leu Leu Gly Thr Ser
            395                 400                 405 ggc ctc aag cgc cgc ttc agc cgc ctg gag aac cgc tac gag gcg ctg        1362
Gly Leu Lys Arg Arg Phe Ser Arg Leu Glu Asn Arg Tyr Glu Ala Leu
        410                 415                 420 gcc aag caa gta gcc tcc gag atg cgc ttc gtg cag gac ctc gtg cgc        1410
Ala Lys Gln Val Ala Ser Glu Met Arg Phe Val Gln Asp Leu Val Arg
    425                 430                 435 gcc ctg gag cag gag aag ctg cag ggc gtg gag tgc ggg ctg cgc            1455
Ala Leu Glu Gln Glu Lys Leu Gln Gly Val Glu Cys Gly Leu Arg
440                 445                 450 taggcgcagt ggggtgggcc aggccccagg acagccggac ctcggcctgc ggtgggggcg     1515
cttcctgtgg acgctgcgcc tcccatcgcc cgggtgcctg tccttgccca gcgccaccag     1575
gctggaggcg gagtgggagg agctggagcc aggcccgtaa gttcgcaggc aggggtgggt     1635
gtgggacggg gctgcttctc tacacagcct ctacgctggc cttcaccttc accctgcat      1695 cgtcggtgac cctgggaccc tccaggcagc gtggcctgtg caccgtgag ggttgggacc      1755 caccgaggcg cagaggcggc ccgaatgcag ccctggttca ggcccggagg agggtttgcg     1815
ggtagttgca cggacaattc ggcggggtgc tgcctgttgc tgccattagc ccaggaggag     1875
gtcgtgggac ggggagggtg ggatggacgg cggacaggca gtccccacgc tgctgggtgg     1935
cgccgggctt ggtggggtct tccactgtgt gcccttctcg ccgaggccgg tccccgggt      1995 gtggggtgcc ctgctgcgga ctcctccgcg agccccatcg tcgcgcctgt ggacgcctag     2055
gcaagagcgg ccctctgcag ccaagagaaa taaaatactg gcttccagat aaaaaaaaaa     2115
aaaaaaaaaa aaaaaaa                                                    2132

<210> SEQ ID NO 4
<211> LENGTH: 1429
<212> TYPE: DNA
<213> ORGANISM: Mus musculus
<220> FEATURE:
<221> NAME/KEY: CDS
<222> LOCATION: (10)..(1353)

<400> SEQUENCE: 4 ccagccgcc atg tcc aca ttc agg caa gag gat gtt gag gac cat tat gag      51
           Met Ser Thr Phe Arg Gln Glu Asp Val Glu Asp His Tyr Glu
           1               5                   10 atg gga gag gag ctt ggc agt ggc caa ttt gcc atc gtg cgc aag tgc        99
Met Gly Glu Glu Leu Gly Ser Gly Gln Phe Ala Ile Val Arg Lys Cys
15                  20                  25                  30 cag cag aag ggc acg ggc atg gag tat gca gcc aag ttc atc aag aag       147
Gln Gln Lys Gly Thr Gly Met Glu Tyr Ala Ala Lys Phe Ile Lys Lys
                35                  40                  45 cgg cgc ctg cca tcc agc cgg cgc ggt gtg agc cgg gag gag atc gaa       195
Arg Arg Leu Pro Ser Ser Arg Arg Gly Val Ser Arg Glu Glu Ile Glu
            50                  55                  60 cgc gag gtg agc atc ctg cgc gag atc cgc cac ccc aac atc ata aca       243
Arg Glu Val Ser Ile Leu Arg Glu Ile Arg His Pro Asn Ile Ile Thr
```

-continued

|  |  |  | 65 |  |  |  | 70 |  |  |  | 75 |  |  |  |  |
|---|---|---|---|---|---|---|---|---|---|---|---|---|---|---|---|
| ctg | cat | gac | gtg | ttc | gag | aac | aag | aca | gat | gtg | gtg | ctg | atc | ctg | gag | 291 |
| Leu | His | Asp | Val | Phe | Glu | Asn | Lys | Thr | Asp | Val | Val | Leu | Ile | Leu | Glu |  |
|  | 80 |  |  |  |  | 85 |  |  |  |  | 90 |  |  |  |  |  |

| ctg | gtg | tcc | ggt | ggc | gag | ctt | ttc | gac | ttc | ctg | gcc | gag | aag | gag | tca | 339 |
| Leu | Val | Ser | Gly | Gly | Glu | Leu | Phe | Asp | Phe | Leu | Ala | Glu | Lys | Glu | Ser |  |
| 95 |  |  |  |  | 100 |  |  |  |  | 105 |  |  |  |  | 110 |  |

| ttg | acg | gag | gat | gag | gcc | acg | cag | ttc | ctc | aaa | caa | atc | cta | gac | ggt | 387 |
| Leu | Thr | Glu | Asp | Glu | Ala | Thr | Gln | Phe | Leu | Lys | Gln | Ile | Leu | Asp | Gly |  |
|  |  |  |  | 115 |  |  |  |  | 120 |  |  |  |  | 125 |  |  |

| gtc | cac | tac | ctg | cac | tcc | aag | cgc | atc | gca | cac | ttt | gac | ctg | aag | ccc | 435 |
| Val | His | Tyr | Leu | His | Ser | Lys | Arg | Ile | Ala | His | Phe | Asp | Leu | Lys | Pro |  |
|  |  |  | 130 |  |  |  |  | 135 |  |  |  |  | 140 |  |  |  |

| gag | aac | atc | atg | ttg | ctg | gac | aag | cac | gca | gcc | agc | ccc | cgc | att | aag | 483 |
| Glu | Asn | Ile | Met | Leu | Leu | Asp | Lys | His | Ala | Ala | Ser | Pro | Arg | Ile | Lys |  |
|  |  | 145 |  |  |  |  | 150 |  |  |  |  | 155 |  |  |  |  |

| ctc | atc | gac | ttt | ggc | atc | gcg | cac | agg | atc | gag | gct | ggc | agc | gag | ttc | 531 |
| Leu | Ile | Asp | Phe | Gly | Ile | Ala | His | Arg | Ile | Glu | Ala | Gly | Ser | Glu | Phe |  |
|  | 160 |  |  |  |  | 165 |  |  |  |  | 170 |  |  |  |  |  |

| aag | aac | atc | ttt | ggc | aca | ccc | gag | ttt | gtc | gcc | ccc | gag | atc | gtg | aac | 579 |
| Lys | Asn | Ile | Phe | Gly | Thr | Pro | Glu | Phe | Val | Ala | Pro | Glu | Ile | Val | Asn |  |
| 175 |  |  |  |  | 180 |  |  |  |  | 185 |  |  |  |  | 190 |  |

| tat | gag | cca | ctt | ggc | ttg | gag | gct | gac | atg | tgg | agc | att | ggc | gtc | atc | 627 |
| Tyr | Glu | Pro | Leu | Gly | Leu | Glu | Ala | Asp | Met | Trp | Ser | Ile | Gly | Val | Ile |  |
|  |  |  |  | 195 |  |  |  |  | 200 |  |  |  |  | 205 |  |  |

| acc | tac | atc | ctc | ctg | agc | gga | gcg | tcc | cca | ttc | ctg | ggc | gag | acc | aag | 675 |
| Thr | Tyr | Ile | Leu | Leu | Ser | Gly | Ala | Ser | Pro | Phe | Leu | Gly | Glu | Thr | Lys |  |
|  |  |  | 210 |  |  |  |  | 215 |  |  |  |  | 220 |  |  |  |

| cag | gag | acg | ctg | acg | aac | atc | tca | gca | gtg | aac | tat | gac | ttt | gat | gag | 723 |
| Gln | Glu | Thr | Leu | Thr | Asn | Ile | Ser | Ala | Val | Asn | Tyr | Asp | Phe | Asp | Glu |  |
|  |  | 225 |  |  |  |  | 230 |  |  |  |  | 235 |  |  |  |  |

| gaa | tac | ttc | agc | agc | acc | agc | gag | ctg | gcc | aag | gac | ttc | atc | cgc | agg | 771 |
| Glu | Tyr | Phe | Ser | Ser | Thr | Ser | Glu | Leu | Ala | Lys | Asp | Phe | Ile | Arg | Arg |  |
|  | 240 |  |  |  |  | 245 |  |  |  |  | 250 |  |  |  |  |  |

| ctg | ctg | gtc | aaa | gac | ccc | aag | agg | agg | atg | acc | atc | gca | cag | agc | ctg | 819 |
| Leu | Leu | Val | Lys | Asp | Pro | Lys | Arg | Arg | Met | Thr | Ile | Ala | Gln | Ser | Leu |  |
| 255 |  |  |  |  | 260 |  |  |  |  | 265 |  |  |  |  | 270 |  |

| gag | cat | tcc | tgg | atc | aag | gtg | cgc | agg | cgc | gag | gac | ggc | gcc | cgg | aag | 867 |
| Glu | His | Ser | Trp | Ile | Lys | Val | Arg | Arg | Arg | Glu | Asp | Gly | Ala | Arg | Lys |  |
|  |  |  | 275 |  |  |  |  | 280 |  |  |  |  | 285 |  |  |  |

| cca | gag | cga | cgg | cgg | ctg | cgc | gcc | gcg | cgc | ctg | cgc | gag | tac | agc | ctc | 915 |
| Pro | Glu | Arg | Arg | Arg | Leu | Arg | Ala | Ala | Arg | Leu | Arg | Glu | Tyr | Ser | Leu |  |
|  |  |  | 290 |  |  |  |  | 295 |  |  |  |  | 300 |  |  |  |

| aag | tcc | cac | tcg | agc | atg | ccg | cgc | aac | acg | agc | tac | gcc | agc | ttc | gag | 963 |
| Lys | Ser | His | Ser | Ser | Met | Pro | Arg | Asn | Thr | Ser | Tyr | Ala | Ser | Phe | Glu |  |
|  |  | 305 |  |  |  |  | 310 |  |  |  |  | 315 |  |  |  |  |

| cgc | ttc | tca | cgc | gtg | ctg | gag | gac | gtg | gcg | gcg | gca | gag | cag | ggg | ctg | 1011 |
| Arg | Phe | Ser | Arg | Val | Leu | Glu | Asp | Val | Ala | Ala | Ala | Glu | Gln | Gly | Leu |  |
|  | 320 |  |  |  |  | 325 |  |  |  |  | 330 |  |  |  |  |  |

| cgc | gag | ctg | cag | cga | ggc | agg | cgc | cag | tgc | cgg | gag | cgc | gtg | tgt | gcg | 1059 |
| Arg | Glu | Leu | Gln | Arg | Gly | Arg | Arg | Gln | Cys | Arg | Glu | Arg | Val | Cys | Ala |  |
| 335 |  |  |  |  | 340 |  |  |  |  | 345 |  |  |  |  | 350 |  |

| ctg | cgc | gcg | gcc | gcc | gag | cag | cgg | gag | gcg | cgc | tgc | cgc | gac | ggg | agc | 1107 |
| Leu | Arg | Ala | Ala | Ala | Glu | Gln | Arg | Glu | Ala | Arg | Cys | Arg | Asp | Gly | Ser |  |
|  |  |  |  | 355 |  |  |  |  | 360 |  |  |  |  | 365 |  |  |

| gca | ggg | cta | ggg | cgc | gac | ctg | cga | cgc | ctg | cgc | acg | gag | ctg | ggg | cgc | 1155 |
| Ala | Gly | Leu | Gly | Arg | Asp | Leu | Arg | Arg | Leu | Arg | Thr | Glu | Leu | Gly | Arg |  |
|  |  |  | 370 |  |  |  |  | 375 |  |  |  |  | 380 |  |  |  |

| acc | gag | gct | ctg | cgc | acg | cgc | gcg | cag | gag | gag | gcg | cgg | gcg | gcg | ctg | 1203 |

```
Thr Glu Ala Leu Arg Thr Arg Ala Gln Glu Glu Ala Arg Ala Ala Leu
        385                 390                 395 ttg ggt gcc ggg ggc ctg aag cgt cgc ctg tgt cgc ctg gag aac cgt      1251
Leu Gly Ala Gly Gly Leu Lys Arg Arg Leu Cys Arg Leu Glu Asn Arg
    400                 405                 410 tac gac gcg cta gcc gct cag gtg gcc gct gag gtg caa ttc gtg cgc      1299
Tyr Asp Ala Leu Ala Ala Gln Val Ala Ala Glu Val Gln Phe Val Arg
415                 420                 425                 430 gac ctg gtg cgt gcg ctg gag cag gaa cgg ctg cag gct gag tgc ggc      1347
Asp Leu Val Arg Ala Leu Glu Gln Glu Arg Leu Gln Ala Glu Cys Gly
                435                 440                 445 gtg cgc taggctgcgg cacccccaga ccccgaccca ccccagaat aaagctgctt        1403
Val Arg tccacgtaaa aaaaaaaaaa aaaaaa                                          1429

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 5
gggaattcgc ggagcaggag gct                                              23

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 6
ggggatccct agggqaccct tttcta                                           26

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 7
gggtcgacca ccatggctta cccatacgat gttccagatt acgctatgtc cacattcagg      60
caa                                                                    63

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence:Synthetic
      oligonucleotide

<400> SEQUENCE: 8
gggtcgacta gcgcacgccg cactcagcct gc                                    32
```

US 6,171,841 B1

DNA CODING FOR SERINE/THREONINE KINASE

This is a divisional application based on U.S. application Ser. No. 09/159,385, filed Sep. 23, 1998, now U.S. Pat. No. 5,958,748, the contents of which are hereby incorporated by reference.

BACKGROUND OF THE INVENTION

1. Field of the Invention

The present invention relates to a serine/threonine kinase, a DNA coding for said kinase, a recombinant vector comprising said DNA, a transformant transformed with said vector, and a process for preparing the serine/threonine kinase.

2. Prior Art

Various signals from the exterior of a cell are transmitted through receptors on the cell surface into the cell and ultimately into the necleus. The signals transmitted into the nucleus activate transcription factors and, as a result, expression of a group of genes is induced or repressed to produce phenotypes such as cell proliferation, differentiation and cell death. Many transcription factors have been cloned and the structure of functional domains have been elucidated: MOLECULAR BIOLOGY OF THE CELL THIRD EDITION, pp. 401–469. These functional domains are known to include leucine zipper, helix-loop-helix and zinc finger structures. Among them, the leucine zipper structure is a motif commonly found in such transcription factors as Jun/Fos, ATF/CREB and C/EBP families and these transcription factors form homo- or hetero-dimers through their leucine zipper structures to control the transcription of specific genes: Hai, T. et al., Proc. Natl. Acad. Sci., USA, 88:3720–3724 (1991).

Recently, it is reported that the leucine zipper structure is also found other functional molecules than the transcription factors (Holzman, L. B. et al., J. Biol. Chem., 269:30808–30817, 1994), suggesting that the leucine zipper structure not only facilitates the binding between transcription factors but also acts generally as a protein-protein interactional domain in cells.

Therefore, identification of molecules interacting with the leucine zipper domain is considered to be useful in analyzing not only new functions of transcription factors but also functions of the leucine zipper structure in other molecules than the transcription factors.

SUMMARY OF THE INVENTION

It is an object of the present invention to provide a serine/threonine kinase, a DNA coding for said kinase, a recombinant vector comprising said DNA, a transformant transformed with said vector, and a process for preparing the serine/threonine kinase.

As a result of their eager studies based on the above described problems, the present inventors have succeeded in isolating a DNA coding for a serine/threonine kinase from cDNA libraries prepared from human placenta and mouse brain and thus completed the present invention.

Accordingly, the present invention is the following recombinant protein (a) or (b):

(a) a protein comprising the amino acid sequence as shown in SEQ ID NO: 1;
(b) a protein comprising an amino acid sequence having one or several amino acids deleted, substituted or added in the amino acid sequence as shown in SEQ ID NO: 1, and exhibiting a serine/threonine kinase activity.

Also, the present invention is the following recombinant protein (c) or (d):

(c) a protein comprising the amino acid sequence as shown in SEQ ID NO: 2;
(d) a protein comprising an amino acid sequence having one or several amino acids deleted, substituted or added in the amino acid sequence as shown in SEQ ID NO: 2, and exhibiting a serine/threonine kinase activity.

Further, the present invention is a DNA coding for said protein. The DNA include, for example, those comprising the base sequence as shown in SEQ ID NO: 3 or 4.

The present invention is also a recombinant vector comprising said DNA.

Still further, the present invention is a transformant transformed with the recombinant vector.

Finally, the present invention is a process for producing a serine/threonine kinase comprising cultivating the transformant in a culture medium and collecting the serine/threonine kinase from the resulting culture.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The present invention will hereinbelow be described in detail with reference to the drawings attached in which:

FIG. 1 shows the results of homology search in amino acid sequence between human ZIP-kinase (SEQ ID NO: 1) and mouse ZIP-kinase (SEQ ID NO: 2);

FIG. 2 shows the results of homology search in amino acid sequence between human ZIP-kinase (SEQ ID NO: 1), mouse ZIP-kinase (SEQ ID NO: 2), human DAP-kinase and mouse DAP-kinase;

FIG. 3 is an electrophoretic photograph showing the results of western blot;

FIG. 6 is a photograph (the form of an organism) showing the results of colony formation in a selective medium;

FIG. 7 is a photograph of NIH3T3 (the form of an organism) showing the form of apoptosis;

FIGS. 9A and 9B are electrophoretic photographs showing the kinase activity of ZIP-kinase; and FIGS. 10A and 10B are photographs (the form of an organism) showing the intracellular localization of ZIP-kinase.

DESCRIPTION OF THE INVENTION

Figure 4:
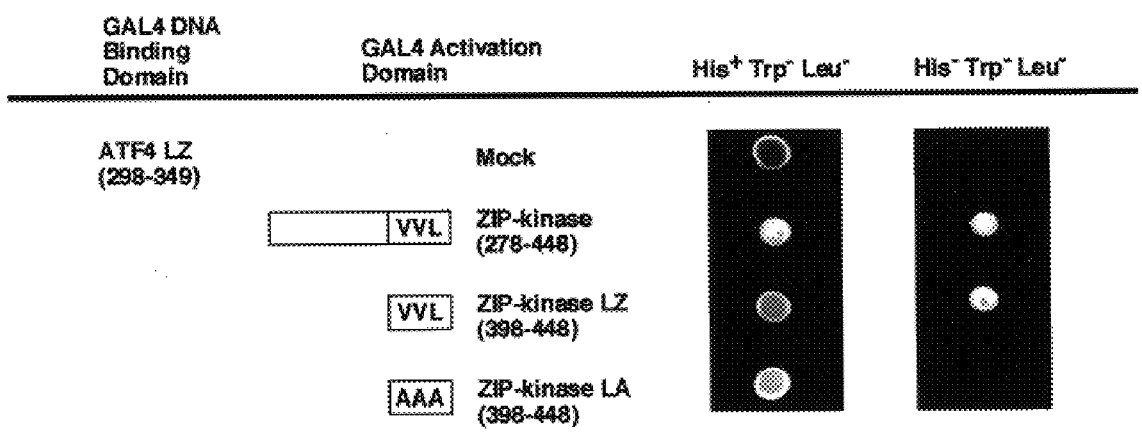
FIG. 4 is a photograph (the form of an organism) showing the results of colony formation in a selective medium.

The recombinant protein according to the present invention, hereinafter also referred to as "ZIP-kinase", is a protein molecule binding to the leucine zipper domain of a transcription factor called ATF4, and has a serine/threonine kinase activity. The ZIP-kinase is a novel nuclear serine/threonine kinase having the leucine zipper structure and has an activity to induce apoptosis. ATF4 is a leucine zipper type transcription factor which binds to cAMP response element (CRE) and belongs to the ATF/CREB family.

On the other hand, the DNA according to the present invention is obtained from cDNA libraries prepared from human placenta and mouse brain by screening them using so-called yeast two-hybrid system, and codes for ZIP-kinase. Hereinafter, the DNA will also be referred to as "ZIP-kinase DNA".

The DNA according to the present invention may be cloned in the following manner:

1. Cloning of ZIP-kinase DNA (1) Preparation of cDNA Libraries from Human Placenta and Mouse Brain Sources of mRNA may include tissues such as human placenta and mouse brain. Established cell lines from these tissues may also be used as the source.

The mRNA may be prepared by conventional procedures. For instance, total RNA may be obtained by treating the tissue or cell with a guanidine reagent, and poly (A+) RNA (mRNA) may be obtained by an affinity column method using oligo dT-cellulose or poly U-Sepharose on Sepharose 2B as a carrier, or by a batch method. Also, the poly (A+) RNA may further be fractionated by sucrose density-gradient centrifugation.

The resulting mRNA is used as a template to synthesize a single-stranded cDNA which is in turn used to synthesize a double-stranded cDNA. A recombinant plasmid is prepared from a suitable vector DNA and used to transform *Escherichia coli* or the like to yield a cDNA library.

Alternatively, the cDNA library may be commercially available (CLONETECH).

(2) Construction of Plasmid pAS2-1

From the cDNA library obtained in (1) above, a plasmid is prepared for screening for a desired clone.

Such a plasmid may be obtained by preparing a chimeric DNA by ligating a DNA coding for mouse ATF4 leucine zipper domain (amino acids 298 to 349 in the sequence of ATF4) to a DNA coding for GAL4 DNA binding domain, and ligating the chimeric DNA to bait plasmid pAS2-1.

(3) Screening

Then said plasmid is used to screen the cDNA library. In the screening, yeast two-hybrid system may be used. The yeast two-hybrid system is an experimental system capable of detecting interaction between proteins in yeast and is capable of screening the library for cDNA of a protein interacting with the desired protein (bait).

Positive clones may be selected using the growth in a selective medium free of hystidine, tryptophan or leucine and the activity of β-galactosidase.

(4) Determination of Base Sequence

The base sequence is determined for the resulting clone. The sequencing may be carried out by any known method such as Maxam-Gilbert method or the dideoxy method and is usually done using an automated base sequencer.

SEQ ID NOs: 1 and 2 exemplify the amino acid sequence of ZIP-kinase and the base sequence of ZIP-kinase DNA, respectively, according to the present invention. As far as a protein comprising said amino acid sequence has an activity as a serine/threonine kinase, there may be a mutation or variation of deletion, substitution and/or addition of one or several amino acids in said amino acid sequence as shown in SEQ ID NO: 1. For example, a protein having the amino acid sequence as shown in SEQ ID NO: 1 from which the first amino acid methionine has been deleted may also be included in the present invention.

Herein the serine/threonine kinase activity means an activity of transferring the terminal phosphate group of ATP to a certain amino acid (serine or threonine) of a protein. The introduction of mutation or variation may be carried out by any known method (Deng, W. P. et al., Anal. Biochem., 200: 81, 1992) or using a commercially available kit (Site-Directed Mutagenesis Kit of CLONETECH).

Once the base sequence of ZIP-kinase DNA according to the present invention is determined, ZIP-kinase DNA according to the present invention may then be obtained by chemical synthesis, or by PCR with various tissues-derived cDNA as a template, or hybridization of a DNA fragment having said base sequence as a probe.

2. Construction of Recombinant Vector and Transformant (1) Construction of Recombinant Vector The recombinant vector of the present invention may be obtained by ligating or inserting ZIP-kinase DNA of the present invention into an appropriate vector. The vector for inserting ZIP-kinase DNA of the present invention is not particularly limited as long as it can be replicated in a host, and may include plasmid DNA, phage DNA, etc. The plasmid DNA may be prepared from *E. coli* or Agrobacterium by the alkali extraction (Birnboim, H. C. & Doly, J., (1979) Nucleic acid Res., 7:1513) or modified method. Further, commercially available plasmids may also be used, for example, pUC18 (Takara Shuzo), pUC19 (Takara Shuzo), pBluescript SK+ (stratagene), pGEM-T (Promega), pT7Blue (Novagen) and PBR322 (Takara Shuzo).

The phage DNA may include, for example, M13mp18, M13mp19, λgt10, λgt11, etc.

When the DNA of the present invention is inserted into a vector, the purified DNA may first be cut with a suitalbe restriction enzyme and inserted into a restriction enzyme site or multi cloning site of a suitalbe vector DNA to ligate with the vector.

The DNA of the present invention should be incorporated into a vector such that the function of the DNA can be realized. In addition to a promoter and the DNA of the present invention, the vector of the present invention may comprise a terminator, a ribosome-binding sequence and the like. The terminator may be a stop codon such as TGA, TAG or TAA and the ribosome-binding sequence may be a leader sequence.

(3) Preparation of Transformant

The transformant of the present invention may be obtained by introducing the recombinant expression vector of the present invention into a host such that the desired gene can be expressed therein.

The host is not particularly limited so long as the DNA of the present invention can be expressed and may include, for example, bacteria belonging to the genus Escherichia or Bacillus, such as *Escherichia coli* and *Bacillus subtillus*; yeast, such as *Saccharomyces cerevisiae* and *Saccharomyces pombe*; animal cells, such as COS and CHO cells; and insect cells, such as Sf9.

When a bacterium, such as *E. coli*, is used as a host, it is preferred that the vector of the present invention is capable of autonomously replicating in said bacterium and comprises a promoter, a ribosome-binding sequence, the DNA of the present invention, and a transcription terminating sequence. The vector may also comprise a gene controlling the promoter.

For example, pET and pGEX (Pharmacia) may be used as the expression vector.

Any promoter may be used so long as the expression can be effected in the host such as *E. coli*. A promoter derived from *E. coli* or phage, such as trp, lac, PL or PR promoter, may be used. An artificially designed and modified promoter, such as T7 or T3, may also be used.

The method for introducing the recombinant vector into a bacterium is not particularly limited so long as a DNA can be introduced into a bacterium. For example, the method using calcium ion (Proc. Natl. Acad. Sci., USA, 69, 2110–2114 (1972)) and the electroporation method may be used.

When a yeast is used as a host, YEp13, YEp24 and YCp50 may be used as the expression vector. The promoter used is not particularly limited so long as the expression in the yeast can be effected, and may include, for example, gal1, gal10, heat shock protein, MFα1 and SV40 promoters.

The method for introducing the recombinant vector into a yeast is not particularly limited so long as a DNA can be introduced into a yeast, and include, for example, the electroporation method (Methods Enzymol., 194, 182–187 (1990)), the spheroplast method (Proc. Natl. Acad. Sci., USA, 84, 1929–1933 (1978)), and the lithium acetate method (J. Bacteriol., 153, 163–168 (1983)).

When an animal cell is used as a host, an expression vector, such as pcDNAI/Amp or pcDNAI (Invitrogen) is used. The promoter used may also be the early gene promoter of human cytomegalovirus.

The method for introducing the recombinant vector into an animal cell may include, for example, the electroporation method, the calcium phosphate method and the lipofection method.

The recombinant vectors of the present invention (one vector containing ZIP-kinase DNA from human placenta and another vector containing ZIP-kinase DNA from mouse brain) have been introduced into *E. coli* DH5, *E. coli* (hZIP-kinase) DH5 and *E. coli* (mZIP-kinase) DH5, respectively, and deposited at National Institute of Bioscience and Human-Technology (NIBH), Agency of Industrial Science and Technology, 1–3, Higashi 1-chome, Tsukuba-shi, Ibaraki-ken 305, Japan on Sep. 25, 1997 under Accession Nos. FERM BP-6487 and FERM BP-6488, respectively.

3. Production of ZIP-kinase

ZIP-kinase of the present invention may be obtained by cultivating the transformant in a culture medium and collecting from the resulting culture.

The transformant of the present invention may be cultivated in a culture medium by any method conventionally used to cultivate a host.

The culture medium for cultivating a transformant obtained from a microorganism such as *E. coli* or yeast as a host may be either a natural or synthetic medium so long as it contains a carbon source, a nitrogen source and inorganic salts which can be utilized by the microorganism and the transformant can efficiently be cultivated.

The carbon source used may include carbohydrates, such as glucose, fructose, sucrose, starch, and dextrose; organic acids, such as acetic acid and propionic acid; and alcohols, such as ethanol and propanol.

The nitrogen source which may be used includes ammonia; ammonium salts of inorganic or organic acids, such as ammonium chloride, ammonium sulfate, ammonium acetate and ammonium phosphate; other nitrogen containing compounds; peptone, meat extract, corn steep liquor, and yeast extract.

The minerals which may be used include monobasic potassium phosphate, dibasic potassium phosphate, magnesium phosphate, magnesium sulfate, sodium chloride, ferrous sulfate, manganese sulfate, copper sulfate, calcium carbonate, calcium chloride, and disodium phosphate.

The cultivation is generally carried out at 37° C. for 12 to 18 hours under aerobic conditions, such as shaking culture and aerated spinner culture. During the cultivation, pH is kept at 7.0 to 7.5. The pH is adjusted with an inorganic or organic acid or alkaline solution, or carbonic acid gas.

During the cultivation, an antibiotic such as ampicillin or tetracycline may optionally be added to the medium.

When a microorganism transformed with an expression vector comprising an inducible promoter is cultivated, an inducer may be added to the medium, if necessary. For example, when a microorganism transformed with an expression vector comprising Lac promoter is cultivated, isopropyl-β-D-thiogalactopyranoside (IPTG) or the like may be added to the medium. When a microorganism transformed with an expression vector comprising trp promoter is cultivated, indole-acrylic acid (IAA) may be added to the medium.

When a transformant obtained from an animal cell as a host is cultivated, a conventional culture medium such as RPMI 1640 or DMEM medium or these media to which fetal bovine serum is added may be used.

The cultivation is generally carried out at 37° C. for 1 to 3 days in the presence of 5% $CO_2$.

During the cultivation, an antibiotic such as kanamycin or penicillin may be added to the medium.

After the cultivation, when ZIP-kinase of the present invention is produced in the host cell, the ZIP-kinase is extracted by disruption of the cell. When ZIP-kinase of the present invention is produced in the exterior of the cell, the culture may be directly used as it is, or the ZIP-kinase of the present invention may be isolated and purified from the culture, after removing the cell by centrifugation, using any conventional biochemical methods generally used in the isolation and purification of proteins, such as ammonium sulfate precipitation, gel chromatography, ion exchange chromatography and affinity chromatography, singly or in any combination thereof.

EXAMPLES

The present invention will be further illustrated by the following examples. However, the scope of the present invention is not limited to these examples.

Example 1

Cloning of ZIP-kinase DNA (1) Preparation of cDNA Library

A commercially available cDNA (CLONETECH) was used in the present invention.

(2) Construction of Plasmid

DNA coding for leucine zipper domain of mouse ATF4 was obtained by PCR method.

The composition of the PCR reaction was 1.0 μg DNA, 10 mM Tris-HCl (pH 8.3), 50 mM KCl, 1.5 mM $MgCl_2$, 0.2 mM dNTP, 0.5 μM primer, and 1 U Taq.

The following primers were used:

```
Sense primer:     5'-GGGAATTCGCGGAGCAGGAGGCT-3'        (SEQ ID NO: 5)
Antisense primer: 5'-GGGGATCCCTAGGGGACCCTTTTCTA-3'    (SEQ ID NO: 6)
```

PCR reaction was first carried out at 94° C. for 1 minute. Then, 25 cycles of reactions at 94° C. for 20 seconds, at 56° C. for 20 seconds and at 72° C. for 30 seconds were carried out. Finally, the reaction at 72° C. for 10 minutes was effected.

The PCR products were cut with EcoRI/BamHI and inserted into EcoRI/BamHI site of pAS2-1 vector. The plasmids were used to transform E. coli DH5α and purified by means of a commercially available kit (Wizard miniprep: Promega) based on alkali-SDS method. This plasmid capable of expressing a fused protein of GAL4 DNA binding domain in yeast was used as a bait.

(3) Screening

Yeast strain Y190 was transformed with the plasmid as a bait using MATCHMAKER Two-Hybrid System kit of CLONETECH. Transformants were selected by growth in tryptophan(−) medium as an index. Further, cDNA libraries capable of expressing a fusion protein with GAL4 transcription activating domain (CLONETECH, mouse brain and human placenta MATCHMAKER cDNA libraries) were transformed. Transformants can grow in tryptophan(−), leucine(−) medium. Further, since reporter genes, HIS3 and LacZ genes, were transcribed if the bait bound to the DNA coding for the protein from the library, positive clones can grow in tryptophan(−), leucine(−), histidine(−) medium and provides blue color in the presence of X-gal because of their β-galactosidase activity. Plasmids were purified from the positive clones using MATCHMAKER Two-Hybrid System kit of CLONETECH, and used to transform E. Coli. Plasmids were purified from the resulting transformants and the base sequences thereof were determined (ABI model 377). The resulting base sequences were searched for homology using GenBank, EMBL, DDBJ data base.

As a result, those having high homology (20% or higher) with the previously reported C/EBP family, AP-1 family and genes having leucine zipper structure were identified as novel genes. Seven (7) and 2 clones of such genes were obtained from mouse brain and human placenta cDNA libraries, respectively. All these genes were derived from an identical gene.

(4) Determination of Base Sequence

The thus obtained gene was considered to code for a kinase and the DNA coding for this novel kinase was designated as ZIP-kinase DNA (Zipper Interacting Protein Kinase DNA). The base sequence of the full length ZIP-kinase DNA was determined.

The base sequences of ZIP-kinase DNA obtained from human placenta and mouse brain are shown in SEQ ID NOs: 3 and 4, respectively. The amino acid sequences encoded by the base sequences of SEQ ID NOs: 3 and 4 are shown in SEQ ID NOs: 1 and 2, respectively.

The amino acid sequence encoded by ZIP-kinase DNA obtained from human placenta (human ZIP-kinase) and the amino acid sequence encoded by ZIP-kinase DNA obtained from mouse brain (mouse ZIP-kinase) were searched for homology therebetween and the leucine zipper domain and serine/threonine kinase domain were found in the C- and N-terminal of the respective amino acid sequences, respectively (FIG. 1). Further, mouse and human ZIP-kinases consisted of 448 and 454 amino acids, respectively, and the homology between mouse and human was 84.9% at amino acid level.

Moreover, the kinase domains of the ZIP-kinases showed high homology with DAP-kinases positively controlling apoptosis caused by IFN-γ, suggesting that these kinases form a new family (FIG. 2).

Example 2

Construction of Recombinant Vector and Preparation of Transformant

To construct a recombinant vector of ZIP-kinase DNA, cDNA coding for ZIP-kinase was synthesized by PCR method.

The PCR reaction mixture and primers used were as follows.

The composition of the PCR reaction was 1.0 μg DNA, 10 mM Tris-HCl (pH 8.3), 50 mM KCl, 1.5 mM MgCl$_2$, 0.2 mM dNTP, 0.5 μM primer, and 1 U Taq.

(SEQ ID NO: 7)

Sense primer: 5'-GGGTCGACCAC CATGGCTTAC CCATACGATG TTCCAGATTA CGCTATGTCC ACATTCAGGC AA-3'

(SEQ ID NO: 8)

Antisense primer: 5'-GGGTCGACTA GCGCACGCCG CACTCAGCCT GC-3'

PCR reaction was first carried out at 96° C. for 1 minute. Then, 30 cycles of reactions at 96° C. for 30 seconds, at 56° C. for 30 seconds and at 72° C. for 1 minute were carried out. Finally, the reaction at 72° C. for 10 minutes was effected.

The resulting PCR products were cut with SalI, inserted into expression vector pEF-BOS (Takara, Ligation kit), and used to transform E. Coli DH5 (TOYOBO). Plasmids were purified from the E. Coli (Promega, Wizard miniprep) and confirmed by DNA sequence (ABI, model 377).

A DNA coding for a variant of ZIP-kinase in which the 42nd amino acid lysine in the amino acid sequence as shown in SEQ ID NO: 2 was changed to alanine, hereinafter referred to as "ZIP-kinase K42A", was constructed by using Site-Directed Mutagenesis Kit of CLONETECH. Also, a DNA coding for another variant in which the 422nd and 429th amino acids valine and the 436th amino acid leucine in the amino acid sequence as shown in SEQ ID NO: 2 were changed to alanines, hereinafter referred to as "ZIP-kinase LA", was similarly constructed.

Example 3

Function of DNA of the Present Invention (1) Binding of ZIP-kinase to ATF4 in Cells Whether ZIP-kinase binds to ATF4 in cells as well or not was investigated.

First, DNA coding for mouse ZIP-kinase (309–448 amino acids in the amino acid sequence as shown in SEQ ID NO: 2) was inserted into expression vector pEF-BOS. Thus, a tag of the transcription factor Myc was provided at the N-terminal end of ZIP-kinase, whereby a DNA coding for Myc-ZIP-kinase complex was designated to have the tag as an epitope to construct the vector (pEF-BOS-Myc-ZIP-kinase). Also, an expression vector (pEF-BOS-FLAG-ATF4) was constructed comprising a DNA coding for human ATF4 (full length)-FLAG complex in which FLAG epitope had been added to the N-terminal end of human ATF4.

These vectors were transiently introduced into COS-7 cell line by the lipofection method and expressed (FIG. 3 in which lanes 1, 4, 7 and 10 represent FLAG-ATF4; lanes 2, 5, 8 and 11 Myc-ZIP-kinase; lanes 3, 6, 9 and 12 FLAG-ATF4 and Myc-ZIP-kinase). 36 hours after the introduction, the cells were collected and solubilized with 0.5% Nonidet P-40 lysis buffer. The resulting solubilized cell (WCE: whole cell extract) was developed in SDS-PAGE, and transferred to nitrocellulose membrane. Western blot analysis was done using anti-FLAG monoclonal antibody (FIG. 3, lanes 1, 2 and 3) and anti-Myc monoclonal antibody (lanes 7, 8 and 9) to confirm the expression of Myc-ZIP-kinase and FLAG-ATF4.

Subsequently, the WCE was immunoprecipitated with anti-Myc monoclonal antibody and the precipitate was subjected to the western blot analysis using anti-FLAG monoclonal antibody, attempting to detect co-immunoprecipitation of Myc-ZIP-kinase and FLAG-ATF4 (FIG. 3, lanes 4 to 6).

As a result, a band of FLAG-ATF4 was detected in lane 6 (FIG. 3). For further confirmation, the WCE was then immunoprecipitated with anti-FLAG monoclonal antibody and the precipitate was subjected to the western blot analysis using anti-Myc monoclonal antibody (lanes 10, 11 and 12). A band of Myc-ZIP-kinase immunoprecipitated with FLAG-ATF4 was found only in lane 12.

Thus, it was shown that ZIP-kinase and ATF4 bind to each other in cells as well.

From this result that ZIP-kinase and ATF4 binds to each other, it may be considered that ATF4 may possibly control the activity of ZIP-kinase.

(2) Determination of Domain Necessary for Binding of ZIP-kinase to ATF4

The site to which ZIP-kinase and ATF4 bind was determined using yeast two-hybrid system. First, variants of mouse ZIP-kinase were prepared: 1) amino acids 278 to 448 of ZIP-kinase (ZIP-kinase 278–448); 2) leucine zipper domain of ZIP-kinase (amino acids 398 to 448) (ZIP-kinase LZ); and 3) a variant of ZIP-kinase in which valine and leucine in the leucine zipper domain were substituted with alanine (ZIP-kinase LA). Each of these variants was designed to produce a chimeric protein with GAL4 trans activating domain, and DNA coding for said chimeric protein was inserted into pACT2 and introduced into yeast strain Y190 together with pAS2-1-ATF4 LZ. The strain was cultivated on histidine+, tryptophan−, leucine−, and histidine−, tryptophan−, leucine− selective media.

Yeast containing DNA coding for ZIP-kinase 278–448 and yeast containing DNA coding for ZIP-kinase LZ could form a colony on the histidine−, tryptophan−, leucine− medium, indicating that ZIP-kinase bound to ATF4 through leucine zipper domain present at the C-terminal (FIG. 4). Further, when valine and leucine in the leucine zipper domain structure were substituted with alanine, the binding to ATF4 was no longer found.

Accordingly, it has been elucidated that ZIP-kinase and ATF4 bind to each other through their respective leucine zipper domain.

(3) Expression of ZIP-kinase in Each Tissue

Northern blot analysis was carried out to investigate the expression of ZIP-kinase in each tissue.

Figure 5:
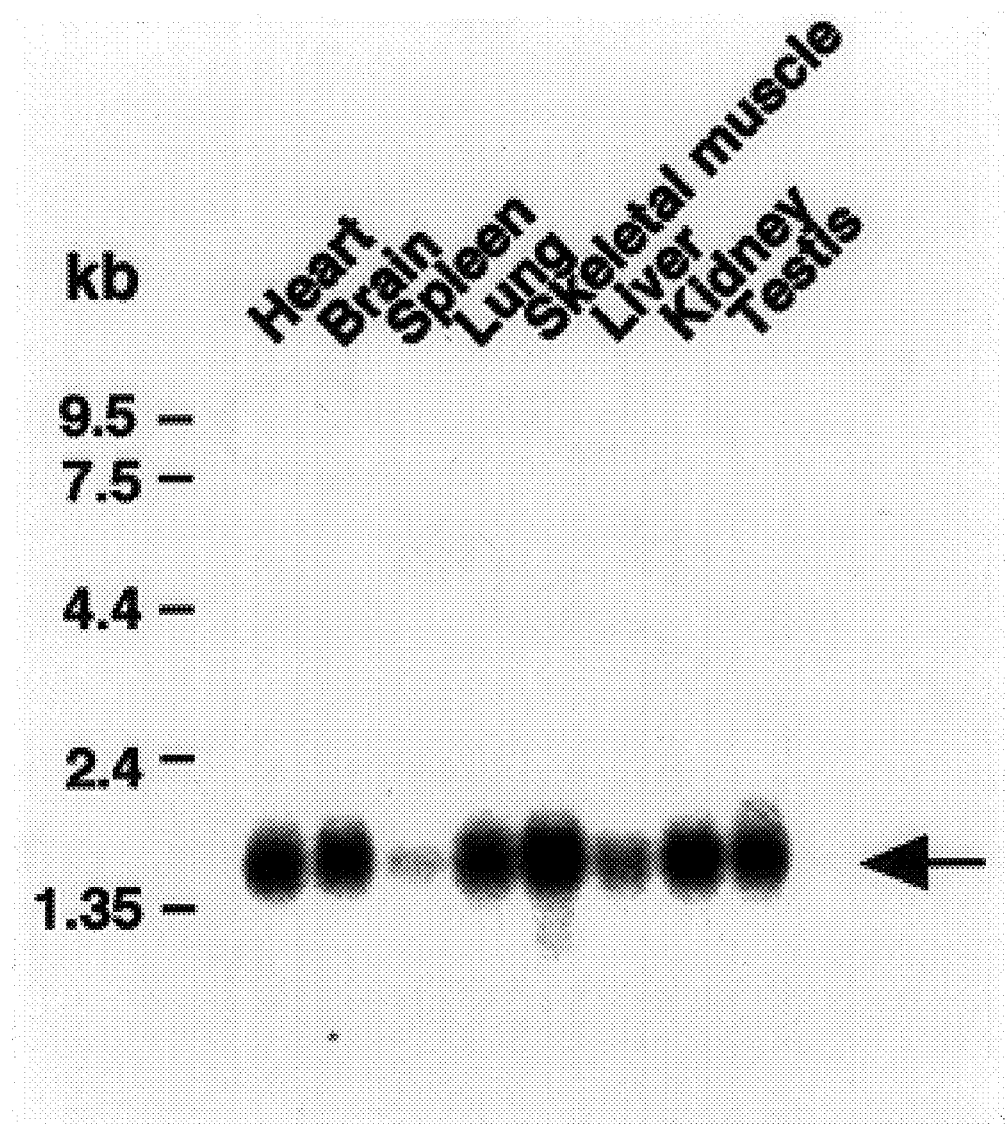
FIG. 5 is an electrophoretic photograph showing the results of northern blot.

As shown in FIG. 5, mRNA of ZIP-kinase (about 1.4 kb) was distributed almost all tissues investigated. However, only low expression was observed in the spleen.

(4) Confirmation of Formation of Homodimer of ZIP-kinase

The leucine zipper domain present at the C-terminal of ZIP-kinase is considered to be a domain through which proteins bind to each other. Whether ZIP-kinase forms a homodimer or not was investigated. Plasmid pAS2-1 into which DNA coding for leucine zipper domain of ZIP-kinase was inserted, and plasmid pACT2 into which DNA coding for the leucine zipper domain of ZIP-kinase and a variant in which valine and leucine in said domain were substituted with alanine, were co-introduced into yeast and colony formation was observed in a selective medium.

As shown in FIG. 6, only yeast co-expressing the ZIP-kinase leucine zipper domain could grow in histidine−, tryptophan−, leucine− medium. Thus, it has been elucidated that ZIP-kinase forms a homodimer through its leucine zipper structure.

(5) Induction of Apoptosis by ZIP-kinase

It has been shown that DAP-kinase, which has high homology with kinase domain of ZIP-kinase, induces apoptosis in HeLa cell. Whether ZIP-kinase has an apoptosis activity was investigated.

RNA wild type ZIP-kinase tagged with HA (pEF-BOS-HA-ZIP-kinase), a variant thereof in which lysine (42nd amino acid), which is present in ZIP-kinase subdomain II and conserved in other kinases, was substituted with alanine (pEF-BOS-HA-ZIP-kinase K42A), and a variant in which valine and leucine in the leucine zipper domain were substituted with alanine (pEF-BOS-HA-ZIP-kinase LA) were prepared, and DNA coding for each of these proteins was transiently introduced into NIH 3T3 cell together with LacZ expression vector (pEF-BOS-LacZ). After 36 hours from the introduction, X-gal staining was effected.

Figure 8:
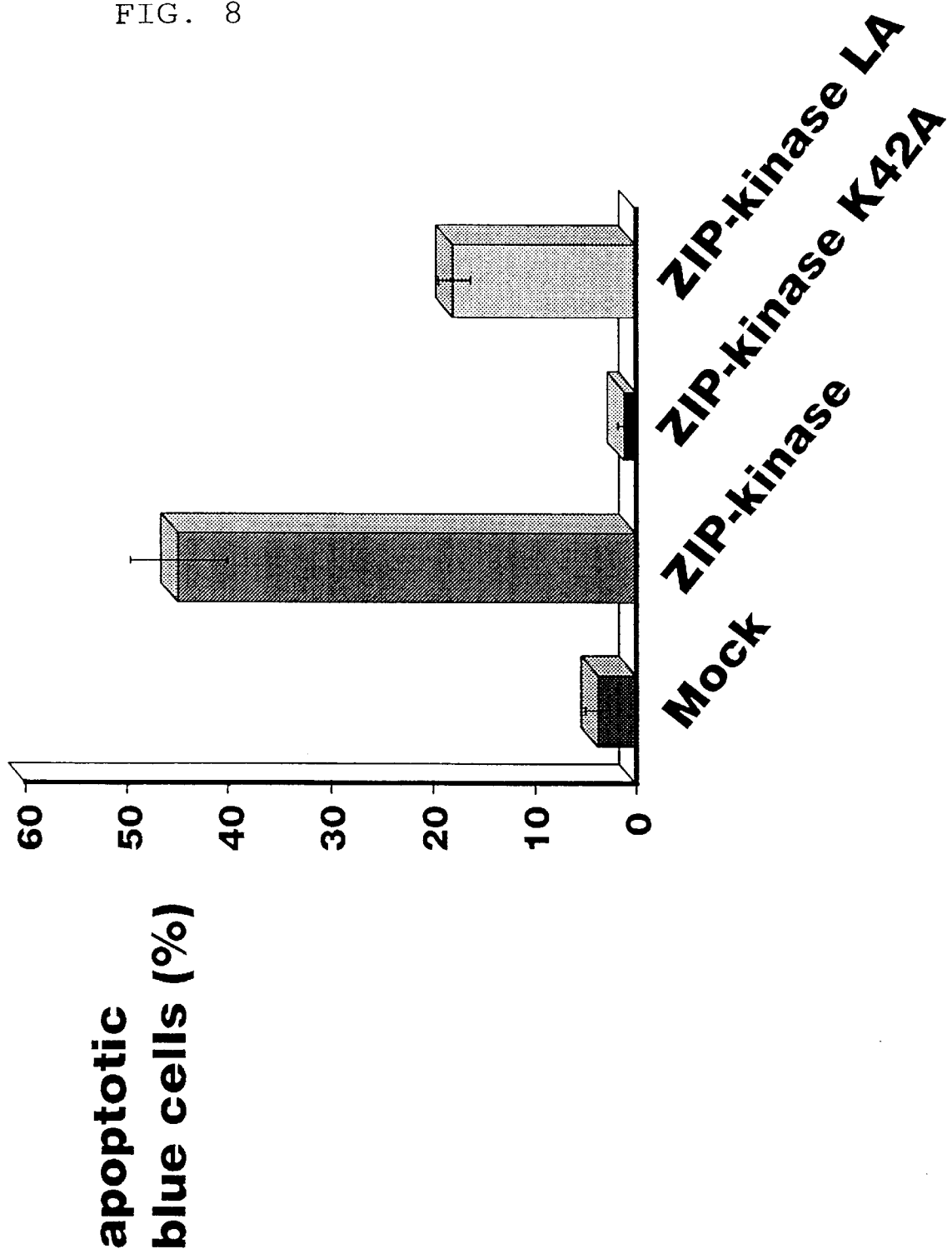
FIG. 8 shows the fraction of LacZ expression cells showing the form of apoptosis.

As a result, a form of cells stained blue was observed under a micorscope (FIG. 7). As compared with a control pEF-BOS-mock (FIG. 7, left, upper), the cell into which the wild type ZIP-kinase was introduced (FIG. 7, right, upper) exhibited a typical form of apoptosis associated with agglomeration of nucleus. The fraction of LacZ expression cells showing the apoptosis form was measured to be 44.9% (FIG. 8).

On the other hand, such change of form was not observed in the ZIP-kinase-K42A variant (FIG. 7, left, lower) and there was no significant difference in the fraction of apoptosis between the vaiant and control. Further, in the ZIP-kinase-LA (FIG. 7, right, lower), some cells caused apoptosis but the fraction thereof was significantly reduced as compared with the wild type.

From the above results, the kinase activity of ZIP-kinase is considered to be essential for the induction of apoptosis by the expression of ZIP-kinase. Further, since apoptosis was suppressed in vatiants in which a homodimer between ZIP-kinases was inhibited, it is suggested that ZIP-kinases form a homodimer to become an activated form.

(6) Kinase Activity of ZIP-kinase

Whether ZIP-kinase indeed has an activity as a kinase was investigated.

Each of pEF-BOS-HA-ZIP-kinase, pEF-BOS-HA-ZIP-kinase K42A, and pEF-BOS-HA-ZIP-kinase LA was transiently introduced into COS-7 cell, and 36 hours later, the cell was collected and solubilized with 0.5% Nonidet P-40 lysis buffer. The solubilized cell was immunoprecipitated with anti-HA monoclonal antibody and the kinase activity in the precipitate was detected by in vitro kinase assay (FIG. 9A).

As a result, a band of phosphorylation by ZIP-kinase was observed at about 50 kDa in the wild type ZIP-kinase (FIG. 9A, lane of HA-ZIP-kinase), while no band corresponding thereto was observed in ZIP-kinase K42A. On the other hand, a phosphorylation band was observed in ZIP-kinase LA. However, when the expression of HA-ZIP-kinase and its variant in the solubilized cell was checked by the western blotting using anti-HA monoclonal antibody, the amount of HA-ZIP-kinase expressed was markedly reduced as compared with the other two variants (FIG. 9B). From this result, it may be considered that the kinase activity observed in ZIP-kinase LA would be very weak as compared with the wild type.

Further, the amount of wild type ZIP-kinase expressed was low in COS-7 cells; this is considered to be resulted from some lethal effect, such as apoptosis, of ZIP-kinase on COS-7 cells.

(7) Localization of ZIP-kinase in Cells

Knowledge of intracellular localization of ZIP-kinase would be considered to be very effective in analyzing the functions of ZIP-kinase. The present inventors have investigated the localization of ZIP-kinase using a confocal laser microscope.

An expression vector (pEF-BOS-FLAG-ATF4) comprising DNA coding for ATF4 tagged with FLAG or another vector (pEF-BOS-FLAG-ZIP-kinase K42A) coding for ZIP-kinase K42A tagged with FLAG was transiently introduced into COS-7 cells. After 36 hours, the cells were fixed, reacted with anti-FLAG monoclonal antibody, and stained using FITC-labelled anti-mouse immunoglobulin antibody as a secondary antibody.

When observed under the confocal laser microscope, the cytoplasm was not stained and the nucleus was stained in the FLAG-ATF4 introduced cells (FIG. 10A). When the localization of FLAG-ZIP-kinase was similarly investigated, the same staining pattern as in ATF4 was observed, confirming that it was localized in the nucleus (FIG. 10B).

Accordingly, it could be concluded that the ZIP-kinase is a novel nuclear serine/threonine kinase.

Advantages of the Invention

According to the present invention, there are provided a serine/threonine kinase, a DNA coding for said kinase, a recombinant vector comprising said DNA, and a transformant transformed with said vector, and a process for the preparation of the serine/threonine kinase.

Since the ZIP-kinase has a function of inducing apoptosis, the ZIP-kinase and DNA coding for said kinase are useful in being utilizable as a gene therapeutical agent against a cancer and as an anti-cancer agent.

What is claimed is:

1. An isolated DNA coding for a protein seleted from the group consisting of:
   (a) a protein comprising the amino acid sequence as shown in SEQ ID NO: 1; and
   (b) a protein comprising an amino acid sequence having the amino acid sequence as shown in SEQ ID NO: 1 in which the first amino acid is deleted.

2. A DNA coding for a protein selected from the group consisting of:
   (a) a protein comprising the amino acid sequence as shown in SEQ ID NO: 2; and
   (b) a protein comprising an amino acid sequence having the amino acid sequence as shown in SEQ ID NO: 2 in which the $42^{nd}$ amino acid residue is changed to alanine; and
   (c) a protein comprising an amino acid sequence having the amino acid sequence as shown in SEQ ID NO: 2 in which the $422^{nd}$, $429^{th}$ and $436^{th}$ amino acid residues are changed to alanines.

3. The DNA of claim 1, comprising the nucleic acid sequence of SEQ ID NO: 3.

4. The DNA of claim 2, comprising the nucleic acid sequence of SEQ ID NO: 4.

5. A recombinant vector comprising a DNA of claim 1.

6. A transformant transformed with a recombinant vector of claim 5.

7. A recombinant vector comprising a DNA of claim 2.

8. A recombinant vector comprising a DNA of claim 3.

9. A recombinant vector comprising a DNA of claim 4.

10. A process for producing a serine/threonine kinase, comprising cultivating a transformant of claim 6 in a culture medium and collecting the serine/threonine kinase from the resulting culture.

* * * * *